(12) United States Patent
Katoh et al.

(10) Patent No.: US 6,589,325 B1
(45) Date of Patent: Jul. 8, 2003

(54) PHTHALOCYANINE COMPOUNDS, WATER-BASE INK COMPOSITIONS AND COLORED PRODUCTS

(75) Inventors: Yoshinori Katoh, Saitama (JP); Hirokazu Kitayama, Saitama (JP); Yasuo Shirasaki, Saitama (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/958,554

(22) PCT Filed: Apr. 25, 2000

(86) PCT No.: PCT/JP00/02696

§ 371 (c)(1),
(2), (4) Date: Oct. 9, 2001

(87) PCT Pub. No.: WO00/64901

PCT Pub. Date: Nov. 2, 2000

(30) Foreign Application Priority Data

Apr. 27, 1999 (JP) ............................................. 11-119248

(51) Int. Cl.$^7$ ........................ C09D 11/00; C09B 47/04; C09B 47/22
(52) U.S. Cl. ................................ 106/31.49; 106/31.78; 540/135
(58) Field of Search ........................... 106/31.49, 31.78; 540/135

(56) References Cited

U.S. PATENT DOCUMENTS

| 5,282,894 | A | * | 2/1994 | Albert et al. ............. 106/31.46 |
| 5,739,319 | A | | 4/1998 | Yamasaki .................... 540/140 |
| 5,759,254 | A | * | 6/1998 | Macpherson et al. ........ 106/410 |
| 5,882,390 | A | * | 3/1999 | Nagai et al. ............. 106/31.49 |
| 6,190,422 | B1 | * | 2/2001 | Carr .............................. 8/445 |
| 6,379,441 | B1 | * | 4/2002 | Kanaya et al. ........... 106/31.49 |
| 6,508,873 | B1 | * | 1/2003 | Shawcross et al. ...... 106/31.49 |

FOREIGN PATENT DOCUMENTS

| EP | 0 173 476 | 3/1986 |
| JP | 3-38587 | 2/1991 |
| JP | 9-77983 | 3/1997 |

* cited by examiner

*Primary Examiner*—Helene Klemanski
(74) *Attorney, Agent, or Firm*—Nields & Lemack

(57) ABSTRACT

An object of the present invention is to provide a novel phthalocyanine compound or the salt thereof as a black colorant that has a hue suitable for ink-jet recording and can provide a recorded material with strong light fastness and water fastness, an ink composition containing the compound, an ink-jet recording method using the ink composition, a tank containing the ink composition, an ink-jet printer set with the tank, and a colored product colored by the colorant.

The novel phthalocyanine compound or the salt thereof can be easily obtained by reacting an aminophthalocyanine with (meth)acrylic acid.

16 Claims, No Drawings

PHTHALOCYANINE COMPOUNDS, WATER-BASE INK COMPOSITIONS AND COLORED PRODUCTS

TECHNICAL FIELD

The present invention relates to a novel phthalocyanine compound, a water-based ink composition containing the salt of the same compound, and a colored product using the same composition.

BACKGROUND OF THE INVENTION

The method for recording by means of an ink-jet printer, a representative method among various color recordings, comprises generating ink droplets and depositing onto various recording materials (such as paper, film, cloth) for recording. The method has rapidly been spread in recent years and will be propagated in future because said ink-jet printer is noiseless as its recording head does not touch a recording material, moreover, said ink-jet printer can be easily downsized, works in a high-speed and gives easy color printing. The water-based ink dissolving a water-soluble dye in a water-based medium has been used as the ink for a fountain pen or a felt pen and ink-jet recording, wherein a water-soluble organic solvent is generally added for the medium so as to prevent ink from clogging at the pen nib or the ink-jet nozzle. The water-based ink is required to privide a satisfactory density of image, not to clog at the pen nib or the ink-jet nozzle, to dry quickly on the recording material, not to blur, and to have good storage stability. The provided image is also required to have satisfactory light fastness and water fastness.

Black ink is the most important among various hues of inks prepared by various dyes because it is used for both a mono-colored image and a full-colored image. The dyes for the black ink have been disclosed by many applications (such as JP Laid-Open No.144067/1980, JP Laid-Open No.207660/1982, JP Laid-Open No.147470/1983, JP Laid-Open No.93766/1984, JP Laid-Open No.190269/1987, JP Laid-Open No.246975/1987, JP Laid-Open No.22867/1988, JP Laid-Open No.33484/1988, JP Laid-Open No.93389/1989, Jp Laid-Open No.140270/1990, JP Laid-Open No.167270/1991, Jp Laid-Open No.200852/1991, JP Laid-Open No.359065/1992, JP Laid-Open No.172668/1994, Jp Laid-Open No.248212/1994, JP Laid-Open No.26 160/1995, and JP Laid-Open No.268256/1995). But there has not yet been provided any black ink to meet satisfactorily the above requirements in the market.

An ink-jet printer is widely used from a small OA printer to a big industrial printer. Therefore, the better water fastness and light fastness in the inks for the said ink-jet printer are strongly required, especially when jetted on a plain paper. However, there has not yet been provided any black ink to meet the requirements in spite of its highest demand. On the other hand, a processed paper, which is remarkably improved in water fastness by coating inorganic particles such as porous silica, alumina sol and a special ceramics absorbing the dye from an ink together with a cationic polymer or a PVA resin on the paper, has been diversely available in the market as a coated paper for the ink-jet printer.

Nevertheless, the water-based black ink is yet inferior to a pigment ink in water fastness. So, it is desired an invention of a black dye and the ink having the same level of water fastness as a pigment ink. The technique to improve its light fastness has not yet been established and it is still remaining as a problem to be solved.

The chemical structure of a black colorant used in a water-based ink for ink-jet recording is represented by an azo product such as a diazo product, a triazo product or a tetrazo product. But an azo product, though it has a relatively good water fastness, is inferior in light fastness to the cyan dye represented by a copper phthalocyanine. So, a water-based black ink is commonly obtained by combining several colorants having the excellent properties respectively.

An object of the present invention is to provide a black colorant and the water-based black ink that, even if used independently, has black hue suitable for ink-jet recording; ranks with a pigment ink in the water fastness and light fastness of a recorded image; and can read a printed bar code by near-infrared ray.

DISCLOSURE OF THE INVENTION

The present inventors made a diligent study to solve the above problem and, as a result, have completed the present invention by finding that a phthalocyanine compound having a carbonyl group, which is a reaction product of an aminophthalocyanine represented by Formula (1) as shown below with (meth)acrylic acid (acrylic acid and/or methacrylic acid, hereinafter in the same meaning to use), or the salt thereof has properties to meet the above object.

Namely, the present invention is as follows:

1. A phthalocyanine compound or the salt thereof obtained by reacting the aminophthalocyanine represented by Formula (1) as shown below with (meth)acrylic acid.

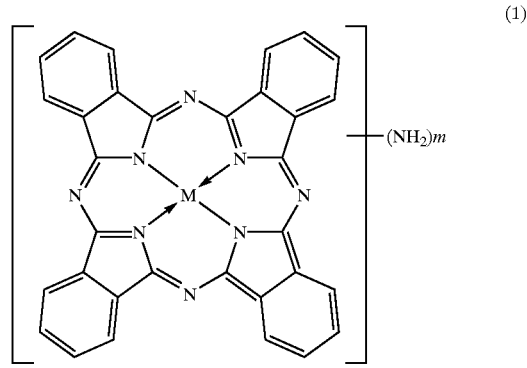

(1)

(In Formula (1), M shows two hydrogen atoms or a metal atom, and m is an integer of 4 or less).

2. An alkali-soluble phthalocyanine compound represented by Formula (3) as shown below or the salt thereof,

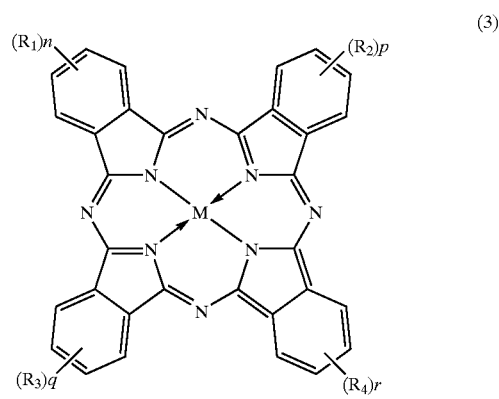

(3)

(In Formula (3), each of $R_1$, $R_2$, $R_3$ and $R_4$ shows independently any one of the groups of NHC2H4COOH, N(C2H4COOH)2, NHCH2CH(CH3)COOH, N(CH2CH(CH3)COOH)2, and NH2; M shows two hydrogen atoms or a metal atom; and each of n, p, q and r shows 0 or 1, provided that n+p+q+r is 1 to 4), which is obtained by reacting an aminophthalocyanine represented by Formula (2) as shown below with (meth)acrylic acid.

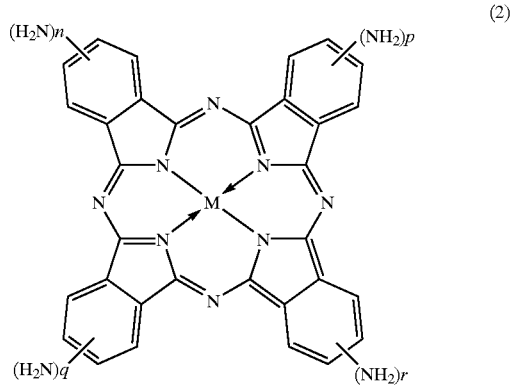

(2)

(In Formula (2), M, n, p, q and r respectively show the same meanings as in Formula (3)).

3. A phthalocyanine compound or the salt thereof according to the above 1 or 2, wherein said metal atom is nickel, copper, zinc, aluminum, iron or cobalt.
4. A phthalocyanine compound or the salt thereof according to the above 3, wherein said metal atom is copper.
5. The salt of a phthalocyanine compound according to the above 2, wherein said salt is an alkali salt having a water-solubility of 2% by mass or more.
6. A water-based ink composition comprising the salt of a phthalocyanine compound according to the above 2.
7. A water-based ink composition according to the above 6, wherein said salt is an alkanolamine salt, a lithium salt, a sodium salt, a potassium salt or an ammonium salt.
8. A water-based ink composition according to the above 6, wherein said salt is an ammonium salt.
9. A water-based ink composition according to the above 6, further comprising water and a water-soluble organic solvent.
10. A water-based ink composition according to the above 6, wherein said water-based ink composition contains 1% by mass or less of inorganic salt.
11. A water-based ink composition according to the above 6, wherein said water-based ink composition is used for ink-jet recording.
12. A method for ink-jet recording which is characterized by using the water-based ink composition according to the above 6 as an ink in said method for ink-jet recording to jet ink droplets on a recording material in response to recording signals.
13. A method for ink-jet recording according to the above 12, wherein said recording material is an information transmission sheet.
14. A tank containing the water-based ink composition according to the above 6.
15. An ink-jet printer set with the tank according to the above 14.
16. A colored product comprising the phthalocyanine compound or the salt thereof according to the above 2.

BRIEF DESCRIPTION OF DRAWINGS

FIG. 1 shows the absorption spectra measured by spectrophotometer of the compounds obtained in Example 1 to 4 of the present invention.

FIG. 2 shows the visible spectra of the starting compound (before the reaction) and the produced compound (after the reaction) in the same solvent in Example 2 of the present invention.

FIG. 3 shows the infrared spectrum of the aminophthalocyanine compound used in Example 2 of the present invention.

FIG. 4 shows the infrared spectrum of the phthalocyanine compound obtained in Example 2 of the present invention.

BEST MODE FOR CARRYING OUT THE INVENTION

A phthalocyanine compound (hereinafter including the salt thereof, unless otherwise specified) of the present invention can be obtained by reacting an aminophthalocyanine with (meth)acrylic acid. The compound is deemed to be a compound produced by the reaction of the amino groups of the aminophthalocyanine with (meth)acrylic acid, practically by the partial or complete conversion of the amino groups binding to the phthalocyanine structure into the carboxyethylamino groups (or carboxymethylethylamino). The novel phthalocyanine compound of the present invention is useful as a novel colorant, especially a black colorant or a black dye because of its good solubility in an alkali aqueous solution and its good fastness in certain conditions.

The phthalocyanine compound of the present invention is considered to contain the compound represented by Formula (3) as the main component and also contain the by-product, a compound resulted from the succeeding reaction of the carboxyl group of the formed phthalocyanine with the vinyl group of (meth)acrylic acid after the reaction of the aminophthalocyanine and (meth)acrylic acid, because a carboxyl group is known to react with a vinyl group. The phthalocyanine compound of the present invention, even if it contains such by-products, is usable for an ink composition.

The phthalocyanine compound of the present invention can be produced, for example, by heating to react the aminophthalocyanine with acrylic acid or methacrylic acid in a solvent. Acrylic acid or methacrylic acid, the starting material of the reaction, may also be used as a solvent. (Meth)acrylic acid as the solvent may be used in an amount necessary to mix under stirring with aminophthalocyanine. The amount is, though not limited to, 3 times or more by mass as much as the aminophthalocyanine, preferably about 3–10 times in view of economy.

The other solvent to use is needed to be fundamentally inert to acrylic acid and methacrylic acid, including, though not limited to, acetic acid, N,N-dimethylformamide, dimethylsulfoxide, and N-methylpyrrolidone. The other solvent may be used in an amount necessary to mix under stirring with aminophthalocyanine, acrylic acid and/or methacrylic acid, and may be used in a small amount if mixed with a large amount of acrylic acid and/or methacrylic acid. The amount is, though not limited to, the same or more by mass as much as the aminophthalocyanine, preferably about 1–8 times. The acrylic acid and/or methacrylic acid to use in this case may be of an amount equal or more in mol to the total amino groups existing in the aminophthalocyanine. The amount is, though not limited to, preferably 2 times or more by mass as much as the aminophthalocyanine, more preferably about 2–10 times in view of reaction velocity to control and reduction of unreacted starting materials.

The reaction is preferably carried out at a temperature to avoid heat-polymerizing acrylic acid or methacrylic acid, for example, at 30° C.–140° C., more preferably at 60° C.–120° C. But the temperature is not limited to the above range, if contamination by polymerization—product of acrylic acid or methacrylic acid is allowed. A known polymerization inhibitor such as methoquinone and hydroquinone may be used to avoid the polymerization. Oxygen gas is likewise effective as the polymerization inhibitor and air can be blown into the reaction system.

The compound thus synthesized is generally a free acid or the salt thereof. The free acid is obtained, for example, by acidic separation. The salt can be converted to the other desirable salt by the usual salt exchange method, for example, by adding the corresponding organic or inorganic base to the free acid of the compound. The organic or inorganic base includes, though not limited to, an alkanolamine (preferably, a C1–C6 mono-, di-, or tri-lower alkanolamine, more preferably a C2–C3 dialkanolamine ) such as diethanolamine and triethanolamine; an alkali metal hydroxide such as lithium hydroxide, sodium hydroxide and potassium hydroxide; ammonium hydroxide; and a water-soluble salt including an alkali metal carbonate such as lithium carbonate, sodium carbonate and potassium carbonate. The reaction product, which cannot be dissolved even by adding an organic or inorganic base, may be filtered. An alkali salt of the phthalocyanine compound of the present invention has preferably a water-solubility of 2% by mass or more, more preferably of 3% by mass or more.

As an insoluble phthalocyanine compound of the present invention in acrylic acid or methacrylic acid is produced by the reaction. Therefore, the filtrate after separating the product is reusable as a solvent for the next reaction.

The produced phthalocyanine compound of the present invention can be detected by the infrared absorption spectrum, because the aminophthalocyanine, a raw material does not have a carbonyl group which shows strongly a maximum absorption in the vicinity of 1700 cm$^{-1}$.

The phthalocyanine compound thus obtained is alkali-soluble, is black and has properties for a black dyestuff, unlikely to the aminophthalocyanine, a raw material. A comprehensive consideration of the physical and chemical properties including the reactivity of the starting material indicates, though not clearly specified only by its physical and chemical properties, however, at least the main reaction product is presumably phthalocyanine compound represented by Formula (3) in view of the comprehensive consideration of the physical and chemical properties including the reactivity of the raw material.

The phthalocyanine compound thus obtained, even if it contains them above by-product or a phthalocyanine compound having an unreduced nitro group which explained afterwards, is included within the range of the present invention as long as it has the performance for a dyestuff of the present invention.

The aminophthalocyanine represented by Formula (1), used for a raw material, can be synthesized by a known method or its modification. For example, according to the known method for the synthesis of a phthalocyanine phthalic anhydride and 4-nitrophthalic acid are used in a proper ratio and are heated to react under the presence of urea and a catalyst (such as a bronze powder) by the known method to synthesize the phthalocyanine having nitro groups, which are then reduced to obtain the aminophthalocyanine. Phthalic anhydride and 4-nitrophthalic acid, if reacted without a metal or a metal salt, gives a compound represented by Formula (1) wherein M shows two hydrogen atoms and, if reacted together with, gives a compound represented by Formula (1) wherein M shows a corresponding metal. The m in Formula (1), though it varies depending on the ratio of phthalic anhydride to 4-nitrophthalic acid, is 4 or less on the average. The aminophthalocyanine may have a coordinated metal at the central position and has generally better fastness to heat and light if it has the coordinated metal. The metal M includes, though not limited to, iron, cobalt, nickel, copper, zinc, aluminium and lead. The aminophthalocynine having copper as the M is used for a raw material for C.I. Sulphur Green 14.

The aminophthalocyanines used as a raw material for the phthalocyanine compound of the present invention can be obtained by reducing the nitro groups of a corresponding nitro compound. By the way, the aminophthalocyanine, even if it has partially the remaining unreduced nitro groups, is allowable to use for a raw material of the phthalocyanine compound of the present invention as long as they give substantially no obstacle to the present invention. The nitro group can be detected by the ESI mass spectrum of the obtained compound.

The water-based ink composition of the present invention is an aqueous solution dissolving the water-soluble salt of the phthalocyanine of the present invention in water or a water-soluble solvent( a water-soluble or water-miscible organic solvent containing water). The water-soluble salt of the phthalocyanine of the present invention suitable for the water-based ink composition has generally a water-solubility of 2% by mass or more, preferably of 3% by mass or more, more preferably of 5% by mass or more. The preferable salt includes an alkanolamine salt, an alkali metal salt and an ammonium salt. The ink has preferably a pH of about 6–11. The water-based ink composition, if used as the ink for an ink-jet printer, contains an inorganic material such as the chloride or sulfate of a metal cation preferably in an amount as little as possible, for example, in 1% or less of the composition. The reaction product can be washed with water to obtain the phthalocyanine compound suitable for a water-based ink composition of the present invention containing little inorganic material. To prepare a colorant of the present invention containing further less inorganic material, the reaction product is desalted, for example, by conventional reverse osmosis or by stirring the dry product or the wet cake of a colorant of the present invention with a mixed solvent of water and alcohol such as methanol, followed by filtering and drying.

The water-based ink composition of the present invention is prepared by using water as a medium. The water-based ink composition contains the phthalocyanine of the present invention or the salt thereof preferably in 0.1–20% by mass, more preferably in 1–10% by mass, and more preferably in 2–8% by mass. The water-based ink composition of the present invention may further contain a water-soluble organic solvent in 0–30% by mass, an ink regulator in 0–5% by mass and water as the remainder.

The ink composition of the present invention is prepared by mixing the compound of the present invention or the salt thereof, if necessary, with a water-soluble organic solvent described below and the additives for preparation of ink, in a pure water such as distilled water. The compound of the present invention or the salt thereof may be dissolved in a mixture of water, the water-soluble organic solvent described below and the additives for preparation of ink. The ink composition of the present invention may be filtered to remove impurities if necessary.

The water-soluble organic solvent includes a C1–C4 alkanol such as methanol, ethanol, propanol, isopropanol (IPA), butanol, isobutanol, secondary butanol and tertiary butanol; a carboxylic amide(preferably a C1–C3 lower carboxylic N-mono- or N,N-di-C1–C3 alkyl amine) such as N,N-dimethylformamide and N,N-dimethylacetoamide; a lactam (preferably a 4–7 membered lactam) such as ε-caprolactam and N-methylpyrrolidin-2-one(N-methyl pyrrolidone); a cyclic urea (preferably a 5–6 membered cyclic urea having optionally a C1–C3 alkyl substituent) such as 1,3-dimetylimidazolidin-2-one and 1,3-dimethylhexahydropyrimid-2-one; a ketone or a keto-alcohol (preferably a C3–C6 ketone or keto-alcohol) such as acetone, methyl ethyl ketone, and 2-methyl-2- hydroxypentan-4-one; a cyclic ether (preferably a 5–6 membered cyclic ether) such as tetrahydrofuran and dioxane; a monomer, oligomer or polymer(polyalkylene glycol or polyalkylene thioglycolate) of alkylene glycol or alkylene thioglycol having C2–C6 alkylene units, such as ethylene glycol, ethylene thioglycol, 1,2- or 1,3-propylene glycol, 1,2- or 1,4-butylene glycol, 1,6-hexylene glycol, diethylene glycol, triethylene glycol, dipropylene glycol, thiodiglycol, polyethylene glycol and polypropylene glycol; a polyol (preferably a C1–C6 triol) such as glycerin and hexane-1, 2,6-triol; an (C1–C4) alkyl ether of polyhydric alcohol (preferably the (C1–C4) alkyl ether of a (C2–C3) polyhydric alcohol having 1–3 hydroxyl groups) such as ethylene glycol monomethyl ether, ethylene glycol monoethyl ether, ethylene glycol monobutyl ether(butyl carbitol), diethylene glycol monomethyl ether, diethylene glycol monoethyl ether, triethylene glycol monomethyl ether, and triethylene glycolmonoethyl ether; γ-butyrolactone; and dimethylsulfoxide.

The additive includes a preservative, a pH adjusting agent, a chelating agent, a rust preventive, a water-soluble ultraviolet absorbing agent, a water-soluble polymeric compound, a dye dissolving agent, a surfactant and other additives for preparation of ink.

The preservative includes sodium dehydroacetate, sodium sorbate, sodium 2-pyridinethiol-1-oxide, sodium benzoate and sodium pentachlorophenol.

The pH adjusting agent includes any substance that can control the ink pH within a range of 6 to 11 as long as it gives no adverse effect on the ink preparation. The examples are alkanolamines such as diethanolamine and triethanolamine; alkali metal hydroxides such as lithium hydroxide, sodium hydroxide, and potassium hydroxide; ammonium hydroxide; or alkali metal carbonates such as lithium carbonate, sodium carbonate and potassium carbonate. The water-based ink composition of the present invention, especially if adjusted in pH with ammonium hydroxide, can provide a printed matter with excellent water fastness because the ammonium ion evaporates as the ammonia into a recording material in printing.

The chelating reagent includes sodium ethylenediaminetetraacetate, sodium nitrilotriacetate, sodium hydroxylethylethylenediaminetriacetate, sodium diethylenetriaminepentaacetate, and sodium uracyl diacetate.

The rust preventive includes acidic hyposulfite salts, sodium thiosulfate, ammonium thioglycolate, diisopropylammonium nitrite, tetranitratepentaerythritol, and dicyclohexylammonium nitrite.

The water-soluble polymeric compound includes polyvinyl alcohol, a cellulose derivative, a polyamine, and a polyimine.

The water-soluble ultraviolet absorbing agent includes sulfonated benzophenone, and sulfonated benzotriazole.

The dye dissolving agent includes ε-caprolactam, ethylene carbonate, and urea.

The surfactant includes an anionic, cationic, or nonionic publicly known surfactant.

A recording material (base material) for ink-jet recording method of the present invention includes an information transmission sheet such as paper and film, fiber and leather. The information transmission sheet is preferably surface-treated and, practically, it has an ink-acceptable layer on the base material. The ink-acceptable layer can be supplied, for example, by impregnating or coating a cationic polymer on the above basement material; or by coating an inorganic fine grain being enable to absorb the dyestuff from an ink such as porous silica, alumina sol and special ceramic together with a hydrophilic polymer such as polyvinyl alcohol and polyvinyl pyrrolidone on a surface of the above basement material. The sheet supplied with the ink-acceptable layer is generally called an ink-jet special paper (film) or a glossy paper (film), and is available on the market, for example, as Pictorico (by Asahi Glass KK), Color BJ Paper, Color BJ Photofilm sheet (by Canon KK), Color Image Jet special paper (by Sharp KK), Superfine special glossy film (by Seiko Epson KK) and Pictafine (by Hitachi Maxell KK). The ink-jet recording method can of course be applied for a plain paper.

The water-based ink composition of the present invention may contain one or more of the other compounds in addition to the phthalocyanine compound of the present invention so as to fit for printing, copying, marking, writing, drawing, stamping, and recording, especially ink-jetting. Such a composition can provide a black printed matter with a high density and a high quality in fastness to water, sun light and abrasion. The phthalocyanine compound of the present invention has higher water fastness and light fastness on a plain paper, especially on a special paper for ink-jet recording.

The water-based ink composition of the present invention brings about no separation by deposition during the storage because of high water solubility. The water-based ink composition of the present invention, if used in an ink-jet printer, brings about no clogging at the jetting nozzles and, even if used for a relatively long time (by a constant recycling or with an intermittent intercept), does not show a change in physical property such as decomposition or lowering color yield.

The tank of the present invention containing the above water-based ink composition. The ink-jet printer of the present invention is what the container of the present invention containing the water-based ink composition is set in the ink-tank section thereof. The colored article of the present invention is what is colored with the above phthalocyanine compound of the present invention or the salt thereof, preferably with the above water-based ink composition.

The water-based ink composition of the present invention has an ideal black color close to the standard in JAPAN COLOR of JNC (Japan Printing Machinery Manufacturers Association), shows the stable black color under various light sources and is excellent in color rendering property. Furthermore, the water-based ink composition of the present invention, if used together with a known magenta, cyan or yellow color having excellent light fastness and water fastness, can provide a color recorded matter with excellent light fastness and water fastness.

The phthalocyanine compound of the preset invention has a high absorption in a near-infrared region and so is suitable for printing a bar code to read by near-infrared ray, effecting the water-based ink composition of the present invention to be very useful.

EXAMPLE

The present invention will be described below in more details with reference to Examples. "part" and "%" in the description are shown by mass unless otherwise specified.

Example 1

20 parts of copper phthalocyanine having an average amino group number per molecule of 3.2 and then 100 parts of acrylic acid were put in a four-neck flask equipped with a condenser, followed by elevating the temperature to 75° C. for 1 hr on an oil bath and stirring at the same temperature for 12 hrs. The reaction solution was cooled down to 40° C. and filtered by a Nutsche funnel to separate the product, which was thoroughly washed with 1000 parts of 60° C. water and dried to obtain 26.2 parts of a black phthalocyanine compound. The compound thus obtained contained inorganic salt in a total amount of 0.4501% (NaCl 0.0391% and Na$_2$SO$_4$ 0.4110%). The ammonium salt of the compound had a water-solubility of 8% and a λ max of 687.2 nm at 0.05 g/1000 ml (in ion-exchanged water).

Example 2

20 parts of copper phthalocyanine having an average amino group number per molecule of 3.2, then 100 parts of acrylic acid and 0.5 parts of hydroquinone were put in a four-neck flask equipped with a condenser, followed by elevating the temperature to 90° C. for 1 hr on an oil bath and stirring at the same temperature for 6 hrs. The reaction solution was cooled down to 40° C. and filtered by a Nutsche funnel to separate the product, which was thoroughly washed with 1000 parts of 60° C. water and dried to obtain 27.9 parts of a black phthalocyanine compound. The compound thus obtained contained inorganic salt in a total amount of 0.0984% (NaCl 0.0320% and Na$_2$SO$_4$ 0.0664%). The ammonium salt of the compound had a water-solubility of 10% and a λ max of 732.8 nm at 0.05 g/1000 ml (in ion-exchanged water).

Example 3

20 parts of copper phthalocyanine having an average amino group number per molecule of 3.2, then 85 parts of acetic acid, 25 parts of acrylic acid and 0.5 parts of hydroquinone were put in a four-neck flask equipped with a condenser, followed by elevating the temperature to 115° C. for 1 hr on an oil bath and stirring at the same temperature for 2 hrs. The reaction solution was cooled down to 40° C. and filtered by a Nutsche funnel to separate the product, which was thoroughly washed with 1000 parts of 60° C. water and dried to obtain 25.9 parts of a black phthalocyanine compound. The compound thus obtained contained inorganic salt in a total amount of 0.8573% (NaCl 0.0333% and Na$_2$SO$_4$ 0.8240%). The ammonium salt of the compound had a water-solubility of 7% and a λ max of 682.8 nm at 0.05 g/1000 ml (in ion-exchanged water).

Example 4

20 parts of copper-coordinating aminophthalocyanine containing unreduced nitro groups obtained by reducing copper phthalocyanine having an average nitro group number per molecule of 4.0, then 100 parts of acrylic acid and 0.5 parts of hydroquinone were put in a four-neck flask equipped with a condenser, followed by elevating the temperature to 90° C. for 1 hr on an oil bath and stirring at the same temperature for 6 hrs. The reaction solution was cooled down to 40° C. and filtered by a Nutsche funnel to separate the product, which was thoroughly washed with 1000 parts of 60° C. water and dried to obtain 32.1 parts of a black phthalocyanine compound. The compound thus obtained contained inorganic salt in a total amount of 0.9120% (NaCl 0.4030% and Na$_2$SO$_4$ 0.5090%). The ammonium salt of the compound had a water-solubility of 10% and a λ max of 750.0 nm at 0.05 g/1000 ml (in ion-exchanged water). The ESI mass spectrum of the compound obtained in Example 4 revealed that it contained the addition product of acrylic acid to an aminophthalocyanine having remaining nitro groups.

The Measurement of Absorption Spectrum

The ammonium salts of the compounds obtained in the above examples were individually dissolved in ion-exchanged water to prepare their 0.05 g/1000 ml of solutions, of which the absorption spectra were measured by UV-2200 spectrophotometer (made by Shimazu Seisakusyo KK). Their absorption spectra are shown in FIG. 1.

The phthalocyanine compound, a raw material used in Example 2 and the ammonium salts of the aminophthalocyanine compound of the present invention obtained in Example 2 were individually dissolved in a mixture solvent (DMF: 2.8% aqueous ammonia=1:1) to prepare their 0.05 g/1000 ml of solutions, of which the absorption spectra were measured in the same way as in FIG. 1. Their absorption spectra are shown in FIG. 2.

The respective infrared absorption spectra of the aminophthalocyanine compound, a raw material used in Example 2 and the phthalocyanine compound of the present invention obtained in Example 2 are shown in FIG. 3 and FIG. 4

The absorption spectra in FIG. 2 reveal that the aminophthalocyanine compound, a raw material, reacted with acrylic acid. From the infrared absorption spectra in FIG. 3 and FIG. 4, it is revealed that there are an alkyl absorption (3000 cm$^{-1}$) and a carbonyl absorption (1700$^{-1}$)in the compound obtained in Example 2 and confirmed that acrylic acid is introduced into the molecule.

Example 5

(A) Preparation of Ink

The solution of the composition as described below was prepared and filtered through a 0.45 μm membrane filter to prepare the water-based ink compositions for ink-jetting. Ion-exchanged water was used. The water-based ink compositions were prepared with water and ammonium hydroxide to have a pH of 8–10 and a total amount of 100 parts.

TABLE 1

| | |
|---|---|
| The colorant obtained in the above Example (Desalted product) | 5.0 parts |
| Glycerin | 5.0 parts |
| Urea | 5.0 parts |
| N-methyl-2-pyrrolidone | 4.0 parts |
| IPA (Isopropyl alcohol) | 3.0 parts |
| Butyl carbitol | 2.0 parts |
| Water and ammonium hydroxide | 76.0 parts |
| Total | 100.0 parts |

The contents of inorganic salt in the water-based ink compositions thus obtained were as follows:

The ink composition containing the compd. of Ex.1: 0.02251%

The ink composition containing the compd. of Ex.2: 0.00492%

The ink composition containing the compd. of Ex.3: 0.04289%

The ink composition containing the compd. of Ex.1: 0.04560%

(B) Ink-jet printing

By using an ink-jet printer (Trade name: PICTY80L, made by NEC KK), ink-jet recordings were done on three kinds of recording paper: a plain paper (Printer Paper A4, TLB5A4S, made by Canon KK), a special paper A (Color BJ Paper LC101, made by Canon KK), a special paper B (Color Image Jet Coat Paper STX73A4, made by Sharp KK). The test results on hue, light fastness, water fastness and color rendering property in recorded images by the water-based ink compositions (containing the compounds of Example 1 to 2) of the present invention are shown in Table 2.

The ink compositions for two comparative examples were prepared so as to coincide in optical density with the black ink of the present invention as in the above (A), but the respective ink compositions contained C.I. Direct Black 19 (represented by following Formula), an azo colorant generally applied for an ink-jet black colorant (Comparative example 1) and the compound (represented by following Formula) described in JP Laid-Open No. 140270/1990 (Comparative example 2) respectively in place of the colorant. The test results on hue, light fastness, water fastness and color rendering property in recorded images pictured by the ink compositions for the comparative examples also are shown in Table 2.

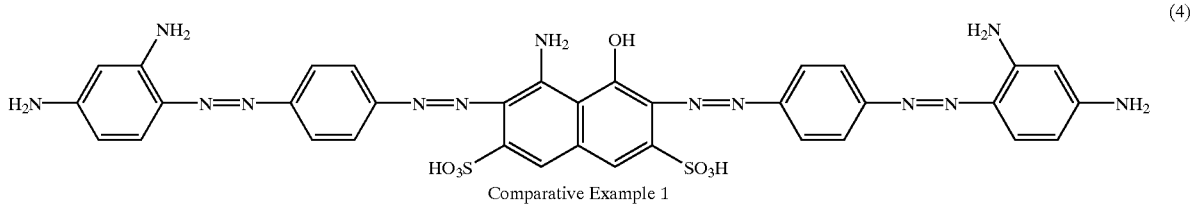

Comparative Example 1 (4)

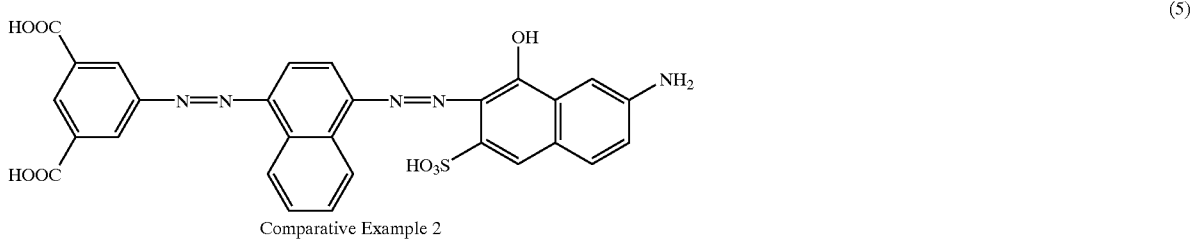

Comparative Example 2 (5)

(C) Evaluation of Recorded Image (1) Hue Determination

Hue and vividness of a recorded image:

The recorded image pictured on a recording material was subject to colorimetry using the GRETAG SPM50 (made by GRETAG KK) to calculate $L^*$, $a^*$ and $b^*$ values.

(2) Light Fastness

A carbon arc fade meter (by Suga Testing Machine KK) was used to irradiate carbon arc on the recorded image for 20 hours. Grade was determined based on blue scale grade as prescribed in JIS L-0841. Color difference ($\Delta E$) between before and after the irradiation also was determined by the above colorimetry system.

(3) Water Fastness

The recorded material was set in a beaker filled with water, stirred for 2 min and air-dried. The change in the recorded image was determined based on the JIS fading gray scale. Color difference ($\Delta E$) between before and after the treatment also was determined by the above colorimetry system.

(4) Color Rendering Property

The deviation in hue of there corded image under a tungsten lamp from under a standard light source was determined by visual observation.

○: a small deviation in hue

Δ: a medium deviation in hue

×: a large deviation in hue

The results in the above (1)–(4) are shown in Table 2.

(5) Reflectance Curve

The recorded image was determined colorimetrically using the COMSEK-V colorimetry system (made by NipponKayaku KK) to draw the reflectance curve. The results of reflectance are shown in Table 3.

TABLE 2

| Recording material | Hue | | | Light fastness Judgment ($\Delta E$) | Water fastness Judgment ($\Delta E$) | Color Rendering property |
|---|---|---|---|---|---|---|
| | $L^*$ | $a^*$ | $b^*$ | | | |
| Example 1 | | | | | | |
| Plain paper | 37.9 | −0.8 | −2.9 | Grade 4 (2.6) | Grade 5 (1.0) | ○ |
| Special paper A | 28.7 | 0.1 | −5.1 | Grade 3–4 (4.5) | Grade 5 (1.9) | ○ |
| Special paper B | 20.3 | −0.5 | −4.5 | Grade 3–4 (4.5) | Grade 5 (0.7) | ○ |
| Example 2 | | | | | | |
| Plain paper | 34.5 | 0.2 | −1.2 | Grade 4 (2.0) | Grade 5 (1.1) | ○ |
| Special paper A | 24.6 | 1.1 | −4.5 | Grade 4 (3.4) | Grade 5 (0.9) | ○ |
| Special paper B | 16.9 | −0.3 | −2.1 | Grade 4 (2.7) | Grade 5 (0.9) | ○ |
| Example 3 | | | | | | |
| Plain paper | 45.2 | −3.8 | −2.3 | Grade 4 (2.3) | Grade 5 (0.9) | ○ |
| Special paper A | 34.4 | −3.3 | −5.3 | Grade 3–4 (3.9) | Grade 5 (2.0) | ○ |
| Special paper B | 28.0 | −4.3 | −5.8 | Grade 3 (6.8) | Grade 5 (1.2) | ○ |
| Example 4 | | | | | | |
| Plain paper | 37.2 | 1.3 | 0.6 | Grade 4 (2.8) | Grade 5 (0.9) | ○ |
| Special paper A | 28.3 | 2.5 | −3.2 | Grade 3 (7.4) | Grade 5 (1.2) | ○ |
| Special paper B | 20.2 | 1.2 | −1.2 | Grade 3–4 (5.7) | Grade 5 (1.5) | ○ |
| Comparative Example 1 | | | | | | |
| Plain paper | 35.6 | −0.1 | −2.3 | Grade 4 (2.0) | Grade 2 (11.5) | ○ |

TABLE 2-continued

| Recording material | Hue L* | a* | b* | Light fastness Judgment (ΔE) | Water fastness Judgment (ΔE) | Color Rendering property |
|---|---|---|---|---|---|---|
| Special paper A | 23.0 | −2.4 | −4.7 | Grade 3–4 (4.1) | Grade 4 (2.9) | ○ |
| Special paper B | 16.4 | −0.5 | −2.3 | Grade 4 (1.5) | Grade 4 (2.8) | ○ |
| Comparative Example 2 | | | | | | |
| Plain paper | 29.2 | 2.9 | −6.9 | Grade 4 (1.3) | Grade 3 (6.2) | Δ |
| Special paper A | 21.9 | 5.4 | −5.6 | Grade 3 (8.0) | Grade 5 (1.0) | Δ |
| Special paper B | 15.6 | 5.1 | −3.3 | Grade 4 (2.8) | Grade 2 (10.3) | Δ |

Table 2 reveals that the ink containing a colorant of the present invention has a black hue by itself and can provide a recorded image which has excellent color rendering property and is very good in water fastness as well as light fastness both on a plain paper and a special paper. Namely, the ink can provide a stable quality in recording on any kinds of recording material including plain paper. On the other hand, the inks containing the azo colorants of Comparative Example 1 and 2 has inferior water fastness on a plain paper and special paper and showed an unstable quality in light fastness depending on the kind of a recording material.

The recorded images provided on the special paper B by the inks containing the compounds of the above Example 1–4, were determined calorimetrically. The results of reflectance versus each wavelength (400–700nm) are shown in Table 3. Table 3 reveals that the phthalocyanine colorant of the present invention shows a black hue by itself.

TABLE 3

| Wave Length (nm) | Example 1 Reflectance (%) | Example 2 Reflectance (%) | Example 3 Reflectance (%) | Example 4 Reflectance (%) |
|---|---|---|---|---|
| 400 | 4.77 | 4.06 | 6.09 | 4.16 |
| 420 | 5.37 | 4.42 | 7.40 | 4.35 |
| 440 | 5.12 | 4.05 | 7.29 | 3.68 |
| 460 | 4.74 | 3.71 | 6.93 | 3.28 |
| 480 | 4.50 | 3.47 | 6.56 | 3.09 |
| 500 | 4.31 | 3.31 | 6.25 | 3.01 |
| 520 | 4.18 | 3.22 | 6.05 | 3.01 |
| 540 | 4.12 | 3.18 | 5.91 | 3.10 |
| 560 | 4.08 | 3.17 | 5.77 | 3.27 |
| 580 | 3.97 | 3.12 | 5.46 | 3.38 |
| 600 | 3.67 | 2.98 | 4.84 | 3.33 |
| 620 | 3.29 | 2.74 | 4.15 | 3.10 |
| 640 | 2.98 | 2.50 | 3.64 | 2.73 |
| 660 | 2.89 | 2.41 | 3.43 | 2.47 |
| 680 | 2.95 | 2.45 | 3.45 | 2.37 |
| 700 | 3.04 | 2.52 | 3.56 | 2.33 |

All the above results reveal that the black ink containing the phthalocyanine colorant of the present invention is an excellent black ink having a wide range of usage.

INDUSTRIAL APPLICABILITY

The phthalocyanine compound of the present invention is useful as a novel colorant excellent in water-solubility, usually shows black color, can be used for a black colorant, and is characterized by having a good filterability through a membrane filter in the production process of an ink composition. Furthermore, the ink composition of the present invention using the phthalocyanine compound does not show a crystal deposition after a long storage, nor a change in physical property and color, so that it has good storage stability. The ink composition of the present invention, when used as a black ink for ink-jet recording, can provide a printed matter with excellence in light fastness and water fastness. Furthermore, the composition also, when used together with a magenta, cyan and yellow dye, can give an ink-jet recorded matter that is excellent in light fastness and water fastness because the composition is close to a pigment in quality. The surface of a printed matter is closely an ideal black and has excellent color rendering property.

Therefore, the ink of the present invention is very useful as a black ink composition for ink-jet recording. The water-based ink composition of the present invention is very effective for printing a bar code to read by near-infrared ray because the phthalocyanine compound of the preset invention has a high absorption in a near-infrared region.

What is claimed is:

1. A phthalocyanine compound or the salt thereof obtained by reacting the aminophthalocyanine represented by Formula (1) as shown below with (meth)acrylic acid

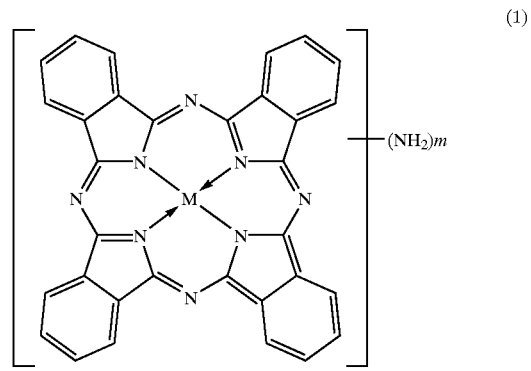

(1)

wherein in Formula (1), M represents two hydrogen atoms or a metal atom, and m is an integer of 4 or less.

2. An alkali-soluble phthalocyanine compound represented by Formula (3) as shown below or the salt thereof,

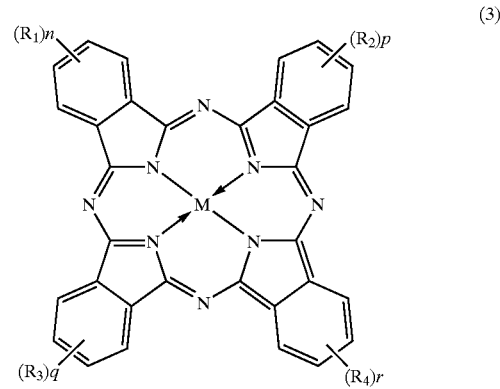

(3)

wherein in Formula (3), each of $R_1$, $R_2$, $R_3$ and $R_4$ independent represents any one of the groups of $NHC_2H_4COOH$, $N(C_2H_4COOH)_2$, $NHCH_2CH(CH_3)COOH$, $N(CH_2CH(CH_3)COOH)_2$, and $NH_2$; M represents two hydrogen atoms or a metal atom; and each of n, p, q and r represents 0 or 1, provided that n+p+q+r is an integer of 1 to 4, which is obtained by reacting an aminophthalocyanine represented by Formula (2) as shown below with (meth) acrylic acid

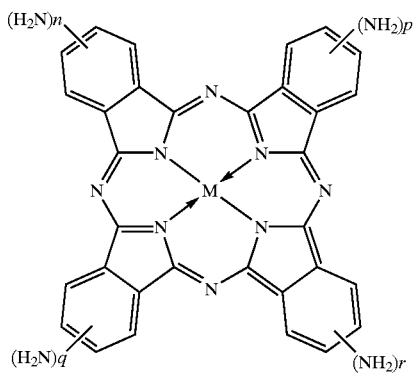

(2)

wherein in Formula (2), M, n, p, q and r respectively show the same meanings as in Formula (3).

3. A phthalocyanine compound or the salt there of according to claim 1 or 2, wherein said metal atom is nickel, copper, zinc, aluminum, iron or cobalt.

4. A phthalocyanine compound or the salt thereof according to claim 3, wherein said metal atom is copper.

5. The salt of a phthalocyanine compound according to claim 2, wherein said salt is an alkali salt having a water-solubility of 2% by mass or more.

6. A water-based ink composition comprising the salt of a phthalocyanine compound according to claim 2.

7. A water-based ink composition according to claim 6, wherein said salt is an alkanolamine salt, a lithium salt, a sodium salt, a potassium salt or an ammonium salt.

8. A water-based ink composition according to claim 6, wherein said salt is an ammonium salt.

9. A water-based ink composition according to claim 6, further comprising water and a water-soluble organic solvent.

10. A water-based ink composition according to claim 6, wherein said water-based ink composition contains 1% by mass or less of inorganic salt.

11. A water-based ink composition according to claim 6, wherein said water-based ink composition is used for ink-jet recording.

12. A method for ink-jet recording which is characterized by using the water-based ink composition according to claim 6 as an ink in said method for ink-jet recording to jet ink droplets on a recording material in response to recording signals.

13. A method for ink-jet recording according to claim 12, wherein said recording material is an information transmission sheet.

14. A tank containing the water-based ink composition according to claim 6.

15. An ink-jet printer set with the tank according to claim 14.

16. A colored product comprising the phthalocyanine compound or the salt thereof according to claim 2.

* * * * *